United States Patent [19] [11] Patent Number: 4,958,017
Fujinawa et al. [45] Date of Patent: Sep. 18, 1990

[54] PURIFICATION OF INOSINE FROM GUANOSINE

[75] Inventors: Shohei Fujinawa, Himeji; Yoshinori Sakamoto, Takasago; Harumasa Iizuka, Kakogawa, all of Japan

[73] Assignee: Takeda Chemical Industries, Ltd., Osaka, Japan

[21] Appl. No.: 283,805

[22] Filed: Dec. 13, 1988

[30] Foreign Application Priority Data

Dec. 17, 1987 [JP] Japan .................................. 62-320743

[51] Int. Cl.$^5$ ..................... C07H 19/167; C07H 19/16
[52] U.S. Cl. ....................................... 536/124; 536/24; 536/26
[58] Field of Search ........................... 536/24, 26, 124

[56] References Cited

PUBLICATIONS

Chemical Abstracts 90:138156v (Sugiyama et al. Jpn. Kokai Tokkyo Koho 78,124,688).
Derwent Abstract Acc. No. 78-88573A/49 (Sugiyama et al. Jpn. Kokai Tokkyo Koho 78,124,688).

Primary Examiner—John W. Rollins
Assistant Examiner—Gary L. Kunz
Attorney, Agent, or Firm—Wenderoth, Lind & Ponack

[57] ABSTRACT

An industrially advantageous process for producing an inosine-guanosine mixture having a higher weight ratio of guanosine/inosine than a starting mixture of nucleoside crystals and inosine subtantially free of guanosine from which comprises adjusting an aqueous fluid containing 10 to 30% by weight/volume of a nucleoside mixture to a pH of 9.1 to 9.5, wherein the total amount of inosine and guanosine is more than 95% by weight based on dry matters and the weight ratio of guanosine/inosine is 0.5 to 1, separating the resultant solids and then crystallizing inosine from the resulting solution.

1 Claim, 5 Drawing Sheets

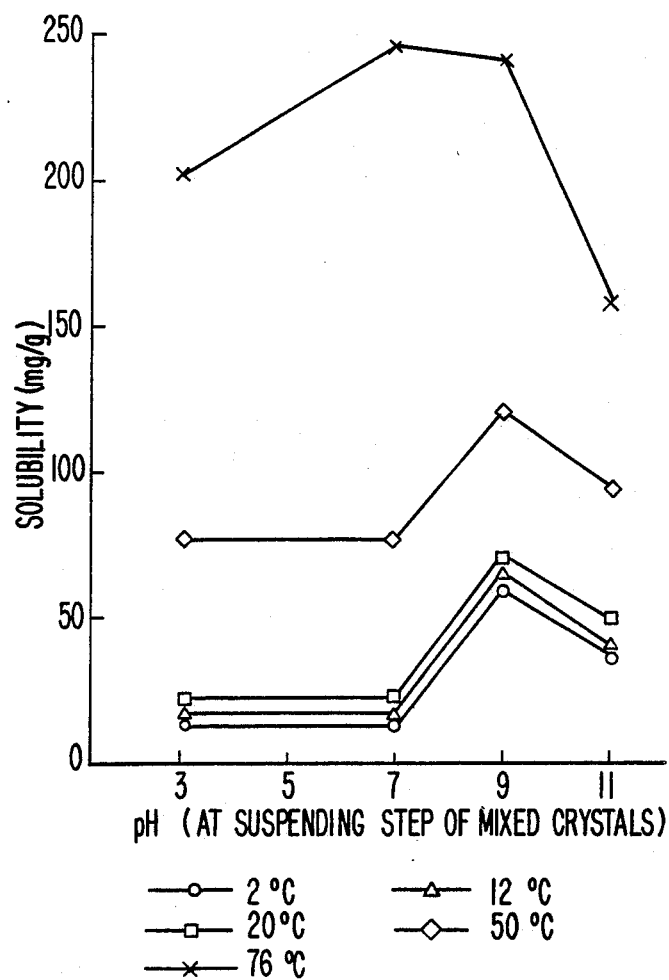

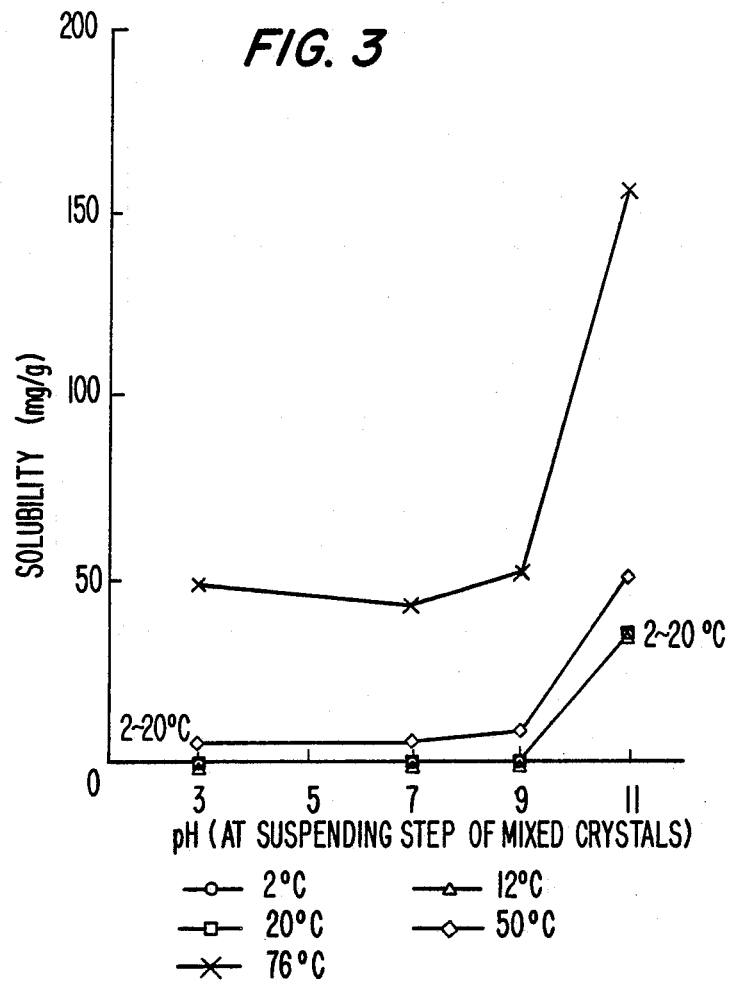

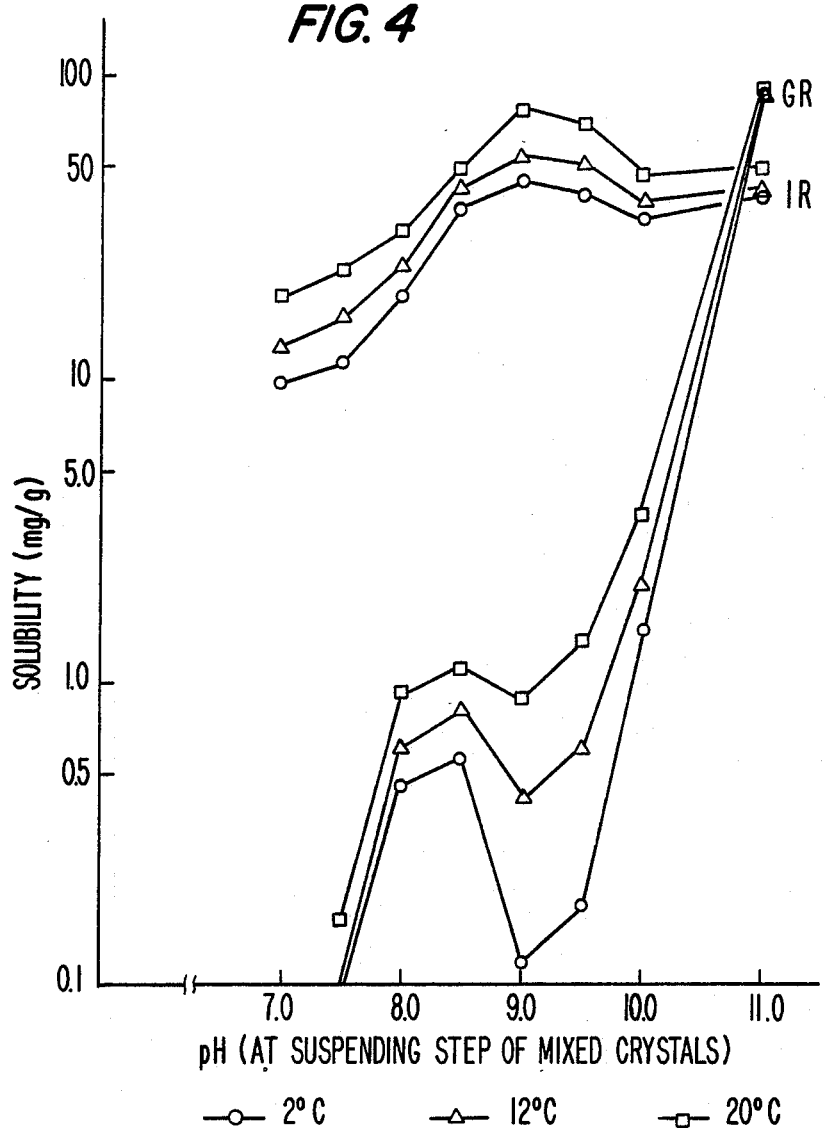

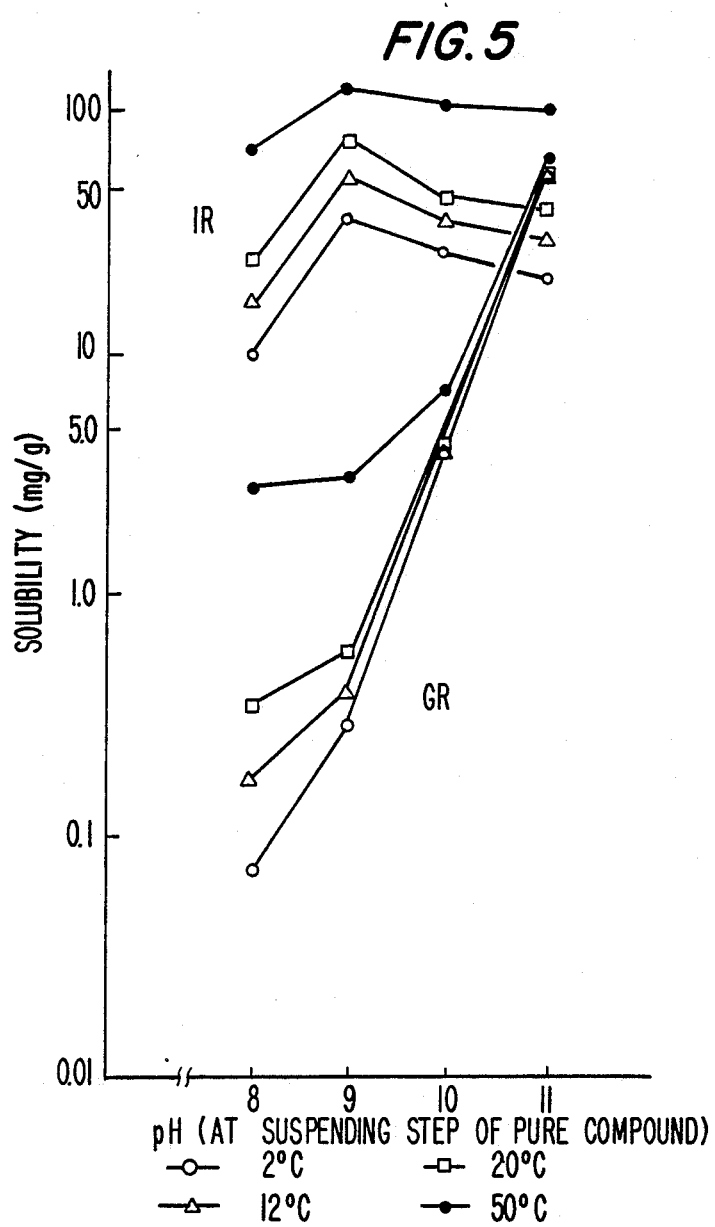

PURIFICATION OF INOSINE FROM GUANOSINE

FIELD OF THE INVENTION

Isosine and guanosine are used as starting materials for the preparation of disodium 5'-isocinate and disodium 5'-guanylate respectively, which are nucleic acid type seasonings, and further as starting materials for the preparation of medicines such as antiviral agents. The present invention relates to a process for producing these nucleosides.

BACKGROUND OF THE INVENTION

Although inosine and guanosine can be produced by a fermentation process, on an industrial scale, it is extremely difficult to produce inosine or guanosine alone by fermentation. Then, usually, there is carried out parallel fermentation wherein both nucleosides are accumulated in amounts of more than 1%, respectively.

If 5'-phosphorylation is carried out by using a starting material containing more than 1.5% of guanosine based on inosine, the content of disodium 5'-guanylate in the resulting crystals of disodium 5'-inosinate becomes more than 1% as that in the starting material, unless a special operation is effected.

Therefore, when inosine or guanosine are produced by nucleoside fermentation in order to obtain disodium 5'-inosinate or disodium 5'-guanylate as a final product, it is important to separate the guanosine or inosine which forms as a concomitant product in the fermentation.

Further, when a mixture containing disodium 5'-inosinate and disodium 5'-guanylate is desired in a specific ration in a final product, for example, a product containing equal weights of these two compounds product, the ratio of guanosine/inosine in a fermented fluid should be always held within a certain range. However, it is also extremely difficult to carry out such fermentation.

In conducting the separation of inosine and guanosine from each other, it has been known that inosine is easily soluble in water, while guanosine is almost insoluble in water [solubility described in The Merck Index, 7th ed., 1960, inosine: f1.6 g/100 ml water (20° C.), guanosine: 1 g/1,320 ml water (18° C.), solubility ratio: about 21-fold]. Based on this fact, there have been established known separation processes such as those described in Japanese Patent Publication No. 56-24519 and the like. Basically, these processes utilize the difference between the water solubilities of the nucleosides. For example, in Japanese Patent Publication No. 56-24519, although the pH in the separation step of these two compounds is limited to 2 to 9, there is merely described that, when the pH is outside the above range, a mineral acid salt or alkali salt is formed.

As described above, by using inosine-guanosine mixed crystals obtained from purification of a fermented fluid as a starting material, the technique for separating it into inosine which is substantially free from guanosine and an inosine-guanosine mixture is of importance from an industrial viewpoint. However, according to a conventional method, when a nucleoside mixture having a high weight ratio of guanosine/inosine, for example a ratio of 0.5 or higher, is simply suspended in water, the weight ratio of guanosine to inosine in the solution considerably exceeds 0.01 (see, Experiment 1 hereinafter and FIG. 1). Thus this method is not satisfactory to obtain inosine substantially free from guanosine.

OBJECTS OF THE INVENTION

Using as starting materials mixed crystals of the nucleosides wherein a weight ratio of guanosine/inosine is 0.5 to 1, the present inventors have intensively searched for an industrial advantageous process for producing inosine substantially free of guanosine and an inosine-guanosine mixture having a higher weight ratio of guanosine/inosine than the starting mixture. During the course of their study, when the pH dependency of the solubility of inosine and guanosine in a suspension of the mixed crystals of the nucleosides in water has been determined, the inventors surprisingly found that inosine shows its maximum solubility at around pH 9. The present inventors have further studied according to this finding, and have attained the present invention.

That is, the main object of the present invention is to provide an industrially advantageous process for producing inosine substantially free of guanosine and an inosine-guanosine mixture having a higher weight ratio of guanosine/inosine than the starting mixture of mixed crystals of the nucleosides.

This object as well as other objects and advantages of the present invention will become apparent to those skilled in the art from the following description with reference to the accompanying drawings.

BRIEF EXPLANATION OF THE DRAWINGS

FIGS. 2 and 3 are graphs illustrating the results of Experiment 2, that is, the relation between pH and solubility of inosine and guanosine when the mixed crystals of inosine and guanosine are suspended in water.

FIG. 4 is a graph illustrating the solubility of inosine and guanosine when the mixed crystals of inosine and guanosine are suspended in water at pH 7 to 10 in Experiment 3.

FIG. 5 is a graph illustrating the relation between pH and solubility of each of inosine and guanosine individually in Experiment 3.

Figure 1:
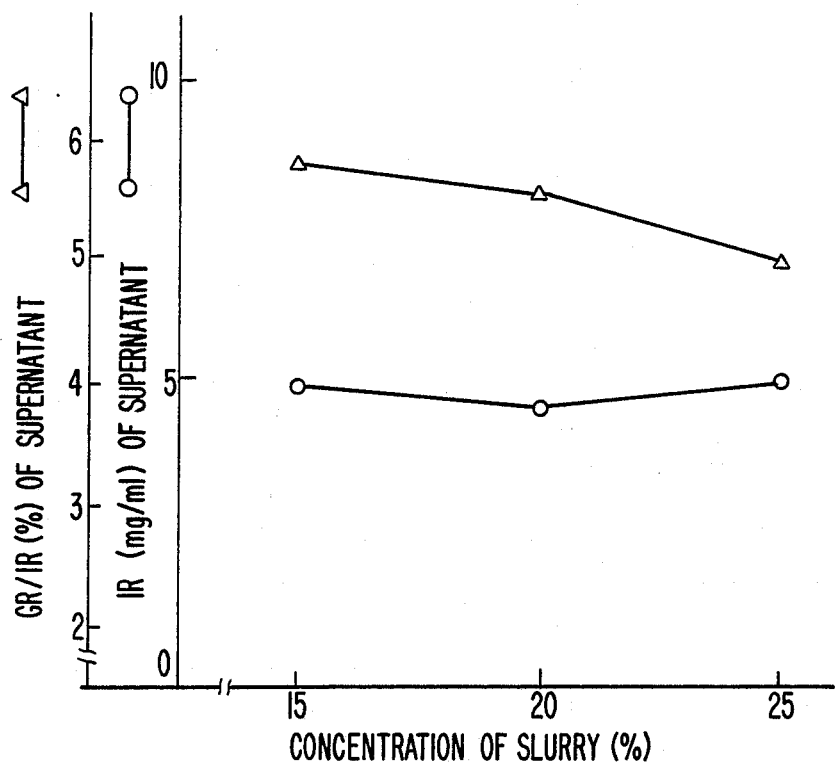
FIG. 1 is a graph illustrating the solubility of inosine in the supernatant obtained in Experiment 1 and the % by weight of guanosine/inosine in the solution.

In the drawings, IR and GR represent inosine and guanosine, respectively.

SUMMARY OF THE INVENTION

According to the present invention, there is provided a process for producing an inosine-guanosine mixture having a higher weight ratio of guanosine/inosine than a starting mixture of nucleosides, and inosine substantially free of guanosine which comprises adjusting an aqueous fluid containing 10 to 30% by weight/volume of a nucleoside mixture to a pH in the range of 9.5, wherein the total amount of inosine and guanosine in the nucleoside mixture is more than 95% by weight based on dry matters and the weight ratio of guanosine/inosine is 0.5 to 1, to separating the resultant solids, and then crystallizing inosine from the resulting solution.

DETAILED DESCRIPTION OF THE INVENTION

Firstly, the relation between solubility and pH of inosine and guanosine from mixed crystals of inosineguanosine is illustrated based on the results of Experiment 2.

As shown in the data in Table 1, e.g. at pH 7, 20° C. in, when the solubilities of inosine and guanosine are measured by using the mixed crystals, the solubility of inosine is higher, while that of guanosine is lower in comparison with the solubilities of the individual compounds disclosed in The Merck Index.

When the relation between solubility and pH in Table 1 is indicated graphically (FIGS. 2 and 3), the solubility curve of guanosine is normal, while that of inosine is notable because it has a maximum solubility at around pH 9. Further, the solubliity of the mixed crystals and the individual pure compounds at around pH 9 are shown in FIGS. 4 and 5. As the result, inosine has a maximum solubility at around pH 9 regardless of the presence of guanosine. On the other hand, guanosine has a minimum solubility at around pH 9 in the presence of inosine, but such a minimum solubility is disappeared in the case of guanosine alone. That is, in Table 1, the remarkable increase in the ratio of inosine/guanosine in the solution when the mixed crystals are suspended at around pH 9 is due to a cooperative effect of the maximum solubility of inosine and the minimum solubility of guanosine.

The finding suggests that, in order to obtain a solution which contains only inosine and substantially no guanosine by suspending inosine-guanosine mixed crystals in water, the pH should be adjusted to around pH 9 and then the solution should be separated.

The, the present inventors have further experimented intensively based upon the above finding and, as a result, have attained the process of the present invention which is extremely advantageous for industrial application because a weight ratio of guanosine/inosine of not more than 0.01 and an extremely great amount of dissolved inosine are obtained by suspending a mixture of inosine and guanosine in water at pH 9.1 to 9.5 as illustrated in Experiment 4. For carrying out the process of the present invention, further specific advantageous conditions are to choose pH 9.4 for the separation of solids at 2° C. and pH 9.2 for the separation at 20° C. as the optimal pH.

Other production conditions of the process of the present invention are illustrated below.

The mixture of inosine and guanosine to be used as a starting material is such that the total amount thereof is not less than 95% by weight based on dry matters and a weight ratio of guanosine/inosine of 0.5 to 1. As to the nucleoside mixture, a mixture can be used which is any known process, for example, a mixture purified and separated from an inosine-guanosine parallel fermented fluid. The mixture is suspended in water within the pH range described above. In this case, by adjusting the concentration to 10 to 30% by weight/volume, the object of the present invention can be attained advantageously. For adjusting pH, an appropriate alkali can be used. Generally, sodium hydroxide is preferred. The aqueous fluid whose pH has been thus adjusted is stirred by an appropriate method, and, generally, warmed to 40° C. or higher, preferably up to 50° to 90° C. to attain the object of the present invention more desirably. That is, this heat treatment is an effective method to adjust the weight ratio of guanosine/inosine in the solution to 0.01 or less. Subsequently, solids are separated from this aqueous fluid. A preferred temperature of this step is generally 20° C. or lower. Separation of solids is carried out according to a conventional method, for example, by centrifugation, filtration and the like. In this case, it is possible to change the ratio of guanosine/inosine in the solids variously by controlling the amount of the solution part to be collected, for example, as shown in Example 4. After separation of the solids, the resulting solution contains inosine which is substantially free from guanosine. In order to obtain inosine from this solution, it is advantageous to employ a process wherein, after adjusting the solution to a pH of about 7, the solution is concentrated until the inosine concentration reaches about 15% by weight/volume, then the solution is adjusted to around pH 5.5, cooled and crystallized. On the other hand, from the solids, there can be obtain a mixture of inosine and guanosine wherein the ratio of guanosine/inosine is h igher than that of the starting mixture.

The present invention is further illustrated by the following examples as well as experimental examples. All %'s used hereinafter are % by weight/weight unless otherwise stated. Inosine and guanosine were determined by using high performance liquid chromatography (manufactured by Shimazu Seisakusho) with resin: CK-10U, solvent: 0.15 M acetate buffer, detection: UV 254 nm.

EXPERIMENT 1

Each of 24.9 g, 35.2 g and 46.9 g portions of mixed crystals composed of 21.1% inosine, 48.9% guanosine and 28.0% water were weighed out and placed in 300 ml round bottom flasks. Then, the flasks were placed in a thermostat bath at 10° C. Into each flask was added 93 ml, 90 ml or 86 ml of water (10° C.) to obtain a suspension (pH=5.7) which were stirred for 2 hours and centrifuged (10,000 G for 10 min.). The supernatant as filtered through Milipore filter (0.45 μ) and the amounts of inosine and guanosine contained in the filtrate were determined. FIG. 1 shows the results of determination of the concentration of each slurry when the mixed crystals were suspended and the amounts of guanosine/inosine (%) and inosine (mg/ml) contained in the supernatant. As seen from this figure, at any slurry concentration, guanosine/inosine (%) in the supernatant is not less than 5% and the amount of residual guanosine is still relatively high. Further, the drawing shows that the concentration of inosine is as low as about 5 mg/ml. Therefore, in order to obtain inosine substantially free from guanosine efficiently, it is apparent that this process would not be satisfactory.

EXPERIMENT 2

Mixed crystals containing 52.3% of inosine and 44.9% of guanosine (150 g) were suspended in water (250 ml). After adjusting to a given pH with hydrochloric acid or sodium hydroxide, the suspension was warmed to 50° C. with stirring. The suspension was cooled at the rate of 10° C./hr. to 2° C. and kept at this temperature for 12 hours. Then, the temperature was raised step by step to 2°, 12°, 20°, 50°, 75° C. and, at each step raising the temperature, sampling was conducted. At each given temperature, the suspension was maintained for 2 hours as an equilibrium period before sampling and, at the step for warming the suspension from 12° C. to 20° C., the starting mixed crystals (20 g) was further added and pH was re-adjusted. Sampling was carried out by putting a syringe with an absorbent cotton plug in the suspension to collect only the solution part and inosine and guanosine were determined by high performance liquid chromatography.

Table 1 shows the relation between solubility of inosine and guanosine in the form of mixed crystals and pH.

The relation between solubilty of inosine and pH is shown graphically in FIG. 2 and the relation between the solubility of guanosine and pH is shown graphically in FIG. 3.

The solubility of guanosine does not change between pH 3 to 9 and it increases at pH 11. On the other hand, the solubility of inosine shows a maximum value at about pH 9. This means that a minimum value of guanosine/inosine is present at about pH 9.

TABLE 1

| Temp. (°C.) | Analytical Value | pH 3.1 | pH 7.0 | pH 9.0 | pH 11.0 |
|---|---|---|---|---|---|
| 2 | IR (mg/g) | 12.1 | 12.1 | 60.7 | 37.0 |
|  | GR (mg/g) | 0.16 | 0.14 | 0.19 | 35.3 |
|  | IR/GR | 75.6 | 86.4 | 319 | 1.1 |
| 12 | IR (mg/g) | 17.3 | 16.5 | 65.9 | 39.8 |
|  | GR (mg/g) | 0.29 | 0.23 | 0.49 | 37.9 |
|  | IR/GR | 59.7 | 71.7 | 134 | 1.1 |
| 20 | IR (mg/g) | 22.5 | 23.1 | 73.3 | 49.7 |
|  | GR (mg/g) | 0.47 | 0.48 | 1.05 | 35.9 |
|  | IR/GR | 47.9 | 48.1 | 69.8 | 1.4 |
| 50 | IR (mg/g) | 77.4 | 78.7 | 123 | 94.3 |
|  | GR (mg/g) | 5.33 | 5.21 | 7.56 | 51.2 |
|  | IR/GR | 14.5 | 15.1 | 16.3 | 1.8 |
| 76 | IR (mg/g) | 204 | 248 | 242 | 160 |
|  | GR (mg/g) | 49.0 | 43.2 | 51.8 | 158 |
|  | IR/GR | 4.2 | 5.7 | 4.7 | 1.0 |

(Note) IR: inosine, GR: guanosine

EXPERIMENT 3

With respect to the mixed crystals containing 48% of inosine, 40% of guanosine and 11% of water, the relation between pH and solubility of inosine and guanosine was determined when the crystals were suspended at pH 7 to 11. The results are shown in FIG. 4.

On the other hand, with respect to pure inosine and guanosine, the relation between pH and solubility when it was suspended was also determined. The results are shown in FIG. 5.

When the mixed crystals are suspended, there is obtained a notable solubility curve which shows that there is a maximum value for inosine and a minimum value of guanosine at about pH 9. On the other hand, in the case of suspending inosine or guanosine alone in water, inosine shows a maximum value similar to that obtained in the presence of both inosine and guanosine (the mixed crystals), whereas the minimum value of guanosine is changed.

The present invention utilizes such a specific solubility obtained only by a suspension wherein both inosine and guanosine are present.

EXPERIMENT 4

By using mixed crystals of inosine and guanosine, according to the same procedure as described in Experiment 2, the relation between pH and solubility of inosine and guanosine was determined when the crystals were suspended at around pH 9. The results are shown in Table 2.

TABLE 2

| Composition of Solution | pH 8.7 | 8.9 | 9.1 | 9.2 | 9.3 | 9.4 |
|---|---|---|---|---|---|---|
| Inosine (mg/g) | 33.2 | 48.3 | 62.5 | 68.0 | 70.6 | 84.7 |
| Guanosine/Inosine (%) | 0.42 | 0.50 | 0.50 | 0.52 | 0.52 | 0.53 |

(Note) Mixed crystals used were composed of 43% of inosine, 39% of guanosine and 16% of water.

In a very narrow pH range of pH 8.7 to about 9.6 the solubility of inosine increases up to a pH of about 9.4 but it decreases at a pH of 9.5 or higher. The value of guanosine/inosine is almost the same at a pH of up to 9.5.

In order to carry out the present invention advantageously on an industrial scale, it can be said that the mixed crystals should be suspended in water at pH 9.1 to 9.5.

EXAMPLE 1

By removing impurities such as cells and the like from a fermented fluid of parallel fermentation of inosine and guanosine, crystallizing and separating a cake from the fluid and air-drying the cake, there were obtained mixed crystals containing 47.0% of inosine, 39.0% of guanosine and 11.6% of water. According to calculation, other impurities were 2.4% based on dry matters.

The air-dried crystals (500 g) were suspended in water (1,700 ml) [suspension concentration: $500 \times 0.86/(1,700 + 500 \times 0.116) = 24\%$ (w/v)], adjusted to pH 9.12 with 10N sodium hydroxide, then warmed to 50° C. in a warm bath and cooled to 2° C. The slurry was separated by a refrigerated centrifuge (10,000 G for 10 min.) and the supernatant was filtered through two sheets of filter paper (No. 5C) to obtain a filtrate (1,150 ml).

The ratio of guanosine/inosine in this filtrate was 0.31%. Thus, the filtrate was purififed to such level that it contained substantially no guanosine in comparison with the ratio in the starting crystals (83%). On the other hand, the weight ratio of guanosine/inosine in the separated and precipitated wet cake became 1.0, i.e., it was increased in comparison with that in the starting crystals (0.83).

The filtrate obtained above was adjusted to pH 7.0 with hydrochloric acid and concentrated under reduced pressure at 60° C. until inosine concentration became 15% (w/v). The concentrate was adjusted to pH 5.5 with hydrochloric acid and a portion thereof (200 ml) was cooled from 60° C. to 2° C. at the rate of 5° C./hr. and the resulting slurry was separated using a fritted-glass funnel (G-3) to obtain crystals of inosine.

The wet crystals of inosine were air-dried overnight and then dried at 100° C. in a vacuum for 5 hours. Analysis of the resulting sample showed that it contained 96.6% of inosine and 0.5% of guanosine and guanosine/inosine was 0.52%. The yield of inosine crystals was 14% (based on inosine in the starting material, i.e., the air-dried mixed crystals).

EXAMPLE 2

Mixed crystals obtained according to the same manner as described in Example 1 (inosine: 52.3%; guanosine: 44.9%; water: 1.2%; impurities according to calculation: 1.6%) (55.8 g) were suspended in water (460 ml) and then pH was adjusted to 9.5 with 5N hydroxide. After warmed at 50° C. for 2.5 hours, the resultant was cooled to 2° C. and only the solution part was obtained from the suspension (cotton plug filtration). In this solution, inosine (46.3 mg/g) and guanosine (0.13 mg/g) were contained and guanosine/inosine was 0.29%. The ratio of guanosine/inosine in the separated residue was 2.5, which was remarkably increased in comparison with that of the starting material (0.86).

EXAMPLE 3

Mixed crystals were obtained by removing impurities such as cells from a fermented fluid which was intentionally contaminated with bacteria during the fermentation operation, crystallizing and separating a cake therefrom and air-drying the cake and two kinds of crystals whose total contents of inosine and guanosine (based on dry matters) was 95.6% and 90.4% were selected. Such mixed crystals were suspended in water (44 g/150 ml), respectively, adjusted to pH 9.11, warmed to 50° C., cooled to 2° C. and separated by a refrigerated centrifuge (10,000 G for 10 min.) to obtain a solution part.

The guanosine/inosine ratios of the solution parts were 0.62% and 6.2%, respectively. The higher value of the latter [(inosine+guanosine) in the starting material was 90.4%] was due to dissolution of guanosine in a high concentration such as 1.1 mg/g. Thus, as the starting material of the present invention, it was considered that the amount of impurities should be of the order of several % (based on dry matters), desirably, not more than 5%.

EXAMPLE 4

Mixed crystals composed of 37.6% of inosine, 31.6% of guanosine and 28.8% of loss on dry ing (water) (14.3 kg) were suspended in water (45.7 liter) and pH was adjusted to 9.22 with sodium hydroxide. The suspension was warmed at 70° C. for 2 hours, then cooled to 20° C. at the rate of 10° C./hr. and subjected to cross flow separation through a ceramic filter with pore size of 0.2 μm (0.179 m²). After separation of the filtrate (40 liter) filtration was continued with the addition of water (hydration filtration) so that the volume of the suspension was maintained at 10 liter to obtain a filtrate hydrated filtrate) (50 liter). The pH of the suspension during this hydration filtration was not adjusted.

Upon this operation, the suspension of the mixed crystals (14.3 kg/45.7 liter of water) was fractionated into three portions, i.e., filtrate, hydrate filtrate and filtered slurry. The material balance during this operation is shown in Table 3.

TABLE 3

Separation of inosine and guanosine (using ceramic filter)

| | Starting Suspension | After Separation | | |
| --- | --- | --- | --- | --- |
| | | Filtrate | Hydrated Filtrate | Filtered Slurry |
| Weight or Volume | 60 kg | 39.1 liter | 50 liter | 16.4 kg |
| Inosine | 5.38 kg (100) | 1.58 kg (29) | 1.01 kg (19) | 2.41 kg (45) |
| Guanosine/Inosine | 83.9% | 0.84% | 3.42% | 184% |
| pH | 9.2 | 8.5 | 8.0 | 7.2 |

That is, as separation (filtration) proceeds, pH of the suspension shifts toward neutral and guanosine/inosine ratio in the filtrate gradually increases. On the other hand, guanosine/inosine in the suspension rapidly increases. When 40 liter of the filtrate is obtained, the operation is stopped so as to keep guanosine/inosine in the filtrate below 1% and, thereby, inosine (29%) is recovered in the filtrate and, at the same time, guanosine/inosine in the slurry remains only 1.3.

Accordingly, by appropriately controlling the collected amount of the filtrate according to this operation, the suspension can be fractionated into inosine portion which is substantially free from guanosine and a portion containing a certain ratio of guanosine/inosine.

In this connection, guanosine content in the inosine crystals obtained by treating the filtrate of Table 3 according to the same manner as described in Example 1 was 0.90%.

By the way, the weight ratio of guanosine/inosine in the hydrated filtrate 3.42% in Table 3 which much exceeds 1% is greatly affected by drop in pH of the suspension below 9 toward neutral or not conducting the warming and cooling steps.

Thus, according to the present invention, inosine substantially free from guanosine as well as a mixture of inosine and guanosine wherein the weight ratio thereof is appropriately adjusted can be advantageously obtained in an industrial scale even by using a mixture of inosine and guanosine wherein the weight ratio of guanosine/inosine is 0.5 to 1, that is, the amount of guanosine is relatively larger. When the treatment is carried out within the pH range specified in the present invention, a large amount of inosine can be transferred to the solution even without completely dissolving the entire nucleoside mixture, i.e., the starting material, which is advantageous from the viewpoint of operation efficiency and energy saving.

What is claimed is:
1. A process for purifying inosine and producing guanosine-inosine mixture from a nucleoside mixture, which comprises:
preparing an aqueous fluid containing 10 to 30% by weight/volume of a nucleoside mixture, said nucleoside mixture having a total amount of inosine and guanosine of more than 95% based on dry weight and a weight ratio of guanosine/inosine of 0.5 to 1,
adjusting the aqueous fluid to a pH of 9.1 to 9.5, warming the aqueous fluid to not lower than 40° C., separating solids containing said guanosine-inosine mixture from the fluid, and
crystallizing inosine from the resulting fluid.

* * * * *